United States Patent [19]

Comer et al.

[11] 4,119,729
[45] Oct. 10, 1978

[54] ALKYLSULFONYLPHENOXYPROPANOLAMINE THERAPEUTIC PROCESS

[75] Inventors: William T. Comer; William E. Kreighbaum, both of Evansville, Ind.

[73] Assignee: Mead Johnson & Company, Evansville, Ind.

[21] Appl. No.: 846,008

[22] Filed: Oct. 27, 1977

Related U.S. Application Data

[60] Division of Ser. No. 722,853, Sep. 10, 1976, Pat. No. 4,067,904, which is a continuation-in-part of Ser. No. 642,638, Dec. 19, 1975, abandoned, which is a continuation-in-part of Ser. No. 455,099, Mar. 27, 1974, abandoned.

[51] Int. Cl.$^2$ ............................................. A01N 9/20
[52] U.S. Cl. ............................ 424/330; 260/340.5 R; 260/343.7; 260/501.17; 260/501.18; 260/501.19; 424/280; 424/282; 424/316
[58] Field of Search ............... 424/316, 280, 330, 282; 260/570.7, 343.7, 501.17, 501.18, 501.19

[56] References Cited

U.S. PATENT DOCUMENTS

| | | | |
|---|---|---|---|
| 3,375,256 | 3/1968 | Bach et al. | 260/570.7 |
| 3,501,769 | 3/1970 | Crowther et al. | 260/501.17 |
| 3,627,832 | 12/1971 | Schulenberg et al. | 260/570.7 |
| 3,631,108 | 12/1971 | Brandstrom et al. | 260/570.7 |
| 3,732,308 | 5/1973 | Lauria et al. | 260/570.7 |
| 4,067,904 | 1/1978 | Comer et al. | 260/570.7 |

OTHER PUBLICATIONS

Derivent Abstracts, "Basic No. 41,107", pp. 357–366 (1969).
Burger, "Medicinal Chemistry" 3rd Ed., p. 77 (1970).

Primary Examiner—Robert V. Hines
Attorney, Agent, or Firm—Robert H. Uloth; Robert E. Carnahan

[57] ABSTRACT

A new class of phenoxypropanolamine alkylsulfonyl derivatives and methods for their preparation are described. The new compounds possess antiarrhythmic and/or cardioselective β-adrenergic blocking properties and are useful in the treatment of hypertension. Representative embodiments of the invention are 1-(isopropylamino)-3-[4-(methylsulfonyl)-m-tolyloxy]-2-propanol and 3-[4-(methylsulfonyl)-m-tolyloxy]-1-(1-phenoxy-2-propylamino)-2-propanol, the latter compound is particularly outstanding as an antihypertensive.

6 Claims, No Drawings

ALKYLSULFONYLPHENOXYPROPANOLAMINE THERAPEUTIC PROCESS

CROSS REFERENCE TO RELATED APPLICATION

This application is a division of U.S. patent application Ser. No. 722,853 and now U.S. Pat. No. 4,067,904 which is a continuation-in-part of U.S. Pat. Application Ser. No. 642,638, filed Dec. 19, 1975 (now abandoned) which in turn is a continuation-in-part of U.S. Pat. Application Ser. No. 455,099, filed Mar. 27, 1974 (now abandoned).

BACKGROUND OF THE INVENTION

This invention pertains to carbon compounds having drug and bio-affecting properties and in particluar to alkylsulfonylphenoxypropylamine β-adrenergic blocking agents.

According to present belief, there are at least two subgroups of β-adrenergic receptors. $\beta_1$-Receptors are thought to mediate cardiac stimulation and $\beta_2$-receptors are supposed to mediate relaxation of smooth muscle responsible for vasodilating and bronchodilating effects; refer to C. G. Dollery, et al., Clinical Pharmacology and Therapeutics, 10(6), 765–799 (1969); D. Jack, The Pharmaceutical Journal, 237–240 (Aug. 29, 1970). Various derivatives of phenoxypropanolamines reportedly have β-adrenergic blocking properties and there can be mentioned as representative of the state of the art, Netherlands Pat. No. 69,07700 (Derwent Basic No. 41,107) and Belgium Pat. No. 762629 (Derwent Basic No. 55533S-B). The Netherlands patent, while generically disclosing pharmaceutical preparations containing a variety of substituted (including alkylsulfonyl) phenoxypropanolamines, does not specifically disclose the class of alkylsulfonylphenoxypropanolamines of the present invention. The Belgium Pat. No. 762,629 describes a group of alkylsulfonylalkylphenoxypropanolamine derivatives.

SUMMARY OF THE INVENTION

This invention relates generally to novel alkylsulfonylphenoxypropylamines which possess cardioselective $\beta_1$-adrenergic blocking and antiarrhythmic properties. More particularly, the present invention provides compounds characterized by general structural Formula I and non-toxic pharmaceutically accceptable acid addition salts thereof.

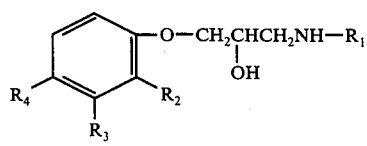

Formula I

In Formula I, $R_1$ represents a branched chain alkyl radical of 3 or 4 carbon atoms such as isopropyl, sec.-butyl, isobutyl and tert.-butyl, phenoxyisopropyl, 4-hydroxy-α,α-dimethylphenethyl, 4-methoxy-β,β-dimethylphenethyl or cycloalkyl of 3 to 6 carbon atoms inclusive; $R_2$ represents hydrogen, lower alkyl, or lower alkylsulfonyl; $R_3$ represents hydrogen or lower alkyl; and $R_4$ represents hydrogen or lower alkylsulfonyl. The compounds of Formula I are further defined in that one and only one of $R_2$ or $R_4$ is lower alkylsulfonyl.

Formulas Ia, Ib, and Ic below and non-toxic pharmaceutically acceptable acid addition salts thereof further characterize the compounds of the invention.

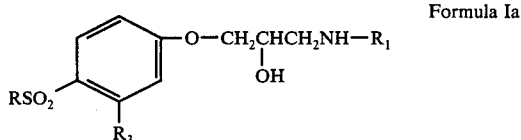

Formula Ia

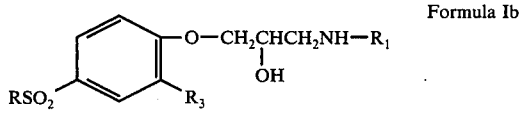

Formula Ib

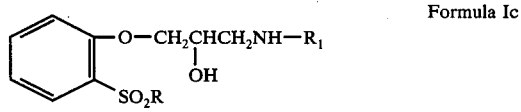

Formula Ic

In Formulas Ia, Ib, and Ic, R is lower alkyl, $R_1$ and $R_3$ are as defined above.

By the term "lower alkyl" as used herein, it is meant that the carbon chain comprising this group include both straight and branched chain carbon radicals of 1 to 4 carbon atoms inclusive. Exemplary of these carbon chain radicals are methyl, ethyl, propyl, isopropyl, 1-butyl, 1-methylpropyl, 2-methylpropyl, and tert.-butyl. As used herein, the term "cycloalkyl" of 3 to 6 carbon atoms inclusive is intended to refer to any of the cycloalkyl radicals of 3 to 6 carbon atoms inclusive such as cyclopropyl, cyclobutyl, cyclopentyl, and cyclohexyl.

The term "non-toxic pharmaceutically acceptable acid addition salts" as used herein refers to salts of compounds of Formula I formed with a variety of relatively non-toxic inorganic or organic acids such as acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzenesulfonic, p-toluenesulfonic, and related acids. The acid addition salts of this invention are prepared in conventional manner by treating a solution or suspension of the free base in a reaction inert organic solvent with the desired acid and then recovering the salts which form by concentration under reduced pressure or by crystallization techniques.

Inasmuch as the compounds of general Formula I possess at least one asymmetric carbon atom, the present invention also includes all possible optically active forms and racemic mixture of the compounds. Resolution of the racemic mixtures to provide the optically active isomers of the compounds of Formula I is carried out by conventional methods relating to resolution of phenethanolamines, for example, by salt formation with an optically active acid such as d-tartaric, dibenzoyl-d-tartaric, d-camphorsulfonic, d-mandelic, etc., followed by fractional crystallization.

According to the present invention, the alkylsulfonylphenoxyamines of Formula I are prepared by a process which comprises reacting a phenol derivative of Formula II

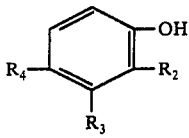

Formula II wherein $R_2$, $R_3$ and $R_4$ have meanings hereinabove described with an epihalohydrin of Formula III

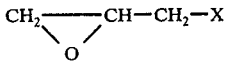

Formula III wherein X signifies halogen, preferably chlorine or bromine, and condensing the epihalohydrin reaction product with an amine of Formula IV $H_2N-R_1$   Formula IV wherein $R_1$ has the meaning hereinabove described; whereafter, if desired, the Formula I product in free base form is reacted with an acid in order to form an acid addition salt.

The Formula II alkylsulfonylphenols are obtained by oxidizing the corresponding alkylthiophenols with hydrogen peroxide in accordance with standard procedures, refer to R. B. Wagner and H. D. Zook, *Synthetic Organic Chemistry*, page 801 (1953 Wiley).

Since an epihalohydrin molecule of Formula III has two reactive positions, reaction with a phenol of Formula II may yield a mixture of Formulas V and VI reaction products wherein $R_2$, $R_3$, $R_4$, and X are as defined above.

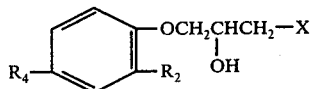

Formula V

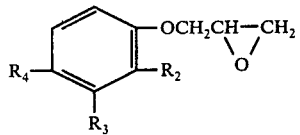

Formula VI

During the further course of the process, however, the two possible intermediates of Formula V and Formula VI on condensation with a Formula IV amine yield the same final product of the present invention. Consequently, it is not necessary to effect a separation of any mixtures of intermediates of Formulas V and VI which may result from interaction of a Formula II phenol with a Formula III epihalohydrin.

If desired, the epihalohydrin reaction product may be taken up in an inert solvent such as chloroform and shaken with excess concentrated hydrochloric acid to convert epoxides of Formula VI into the corresponding Formula V sulfonylphenoxyhalohydrin. Conversely, if desired, the halohydrins of Formula V may be converted to the corresponding Formula VI epoxide in conventional manner, e.g., by treatment with base according to the procedure of O. Stephenson, J. Chem. Soc., 1574 (1954).

The interaction of Formula II phenols with Formula III epihalohydrins is carried out employing an excess of the epihalohydrin and a catalytic amount of a base catalyst such as N-benzylisopropylamine hydrochloride or pyrrolidine base. Other catalysts such as pyridine, piperidine, piperidine acetate, or piperidine hydrochloride are about equally effective.

Interaction of Formula II phenols with Formula III epihalohydrins can also be effected in basic medium, e.g., sodium hydroxide, at ambient temperatures according to the procedure of Y. M. Beasley, et al., J. Pharm. Pharmacol., 10, 47-59 (1958).

Condensation of the epihalohydrin reaction product with a Formula IV amine is carried out preferably in an organic solvent inert under the reaction conditions, e.g., ethanol, toluene, dioxane. The condensation can also be effected in the absence of a reaction solvent by using excess amine such as isopropylamine or tert.-butylamine.

For higher molecular weight amines such as phenoxyethylamine, phenoxy-t-butylamine and the like, equimolar amounts of the reactants are operable and a reaction solvent is not required.

According to a further feature of the present invention, an alternate method for producing compounds of Formula I comprises reacting a Formula II phenol with a compound of Formula VII in alkaline medium

Formula VII to provide a compound of Formula VIII

Formula VIII wherein $R_1$, $R_2$, $R_3$ and $R_4$ have the same meaning as in Formula I and $R_5$ stands for a hydrogenolysable radical such as benzyl or benzhydryl; and converting said compound of Formula VIII to an alkylsulfonylphenoxyamine of Formula I. Removal of the hydrogenolysable blocking group may be effected by catalytic hydrogenation, for example by hydrogenation in the presence of palladium-on-charcoal catalyst, in an inert solvent, e.g., ethanol or aqueous ethanol.

The compounds of Formula VII may be obtained according to known methods. For example, 1-[(N-benzyl)isopropylamino]-2,3-epoxypropane is obtained by reaction of N-benzylisopropylamine and epichlorohydrin in alkaline medium (e.g., aqueous potassium hydroxide) as described by L. Villa, et al., Farmaco., Ed. Sci., 24(3), 349-357 (1969).

A preferred group of alkylsulfonylphenoxyamines of the present invention comprises compounds of Formula IX Formula IX wherein specific values for R, $R_1$, and $R_3$ are those defined above. Specific alkylsulfonylphenoxyamines which fall within the scope of the preferred group are, for example, 1-(isopropylamino)-3-[4-(methylsulfonyl)-m-tolyloxy]-2-propanol,
1-(tert.-butylamino)-3-[4-(methylsulfonyl)-m-tolyloxy]-2-propanol,
1-(isopropylamino)-3-4-(methylsulfonyl)phenoxy-2-propanol,
1-(tert.-butylamino)-3-4-(methylsulfonyl)phenoxy-2-propanol.

A still further preferred group of compounds of Formula IX are those wherein $R_1$ is limited to isopropyl and tert.-butyl radicals and R is limited to the methyl radical.

Cardioselective $\beta_1$-adrenergic blocking activity of the compounds of the present invention can be assessed in standard in vitro pharmacological test systems such as the spontaneously beating rabbit atrial preparation and the guinea pig tracheal preparation. The following Table 1, which compares potency ratios of 1-(isopropylamino)-3-[4-(methylsulfonyl)-3-tolyloxy]-2-propanol hydrochloride and the clinically useful $\beta$-adrenergic receptor antagonist propranolol, is illustrative of the cardiac selectivity of the compounds of the present invention.

Table 1.

| Compound | Potency Ratio Atria | Potency Ratio Trachea | Cardio-selectivity Ratio: Atria/Trachea |
|---|---|---|---|
| Propranolol | 1 | 1 | 1 |
| 1-(Isopropylamino)-3-[4-(methylsulfonyl)-3-tolyloxy]-2-propanol hydrochloride | 0.37 | 0.01 | 37 |

A preferred compound of this invention, 1-(isopropylamino)-3-[4-(methylsulfonyl)-3-tolyloxy]-2-propanol hydrochloride, inhibits increased contractile force and heart rate in the anesthetized dog induced by a standard challenge dose of 0.2 mcg./kg. (intravenous) of isoproterenol when intravenously administered at an $ED_{50}$ of 0.71 mg./kg. body weight and 2.02 mg./kg. body weight respectively.

Another important property of the compounds of the invention is that they have little toxicity in mammals. With 1-(isopropylamino)-3-[4-(methylsulfonyl)-m-tolyloxy]2-propanol hydrochloride, for instance, oral $LD_{50}$ values in the mouse and rat are 1504 and 1792 mg./kg. body weight respectively; the intraperitoneal $LD_{50}$ value in the mouse is 339 mg./kg. body weight.

Substances of the present invention represented by Formula I and Formula X below are novel compositions useful in the prophylaxis and treatment of heart diseases such as angina pectoris, cardiac arrhythmias, cardiovascular anxiety (neurasthenia) and hypertension. The Formula I alkylsulfonylphenoxyamines and particularly those of Formula IX are of value in the treatment of heart diseases because they possess selective $\beta_1$-adrenergic blocking activity. Compounds exhibiting this selective action preferentially block cardiac inotropic and chronotropic action of catecholamines such as epinephrine and isoproterenol without greatly affecting the $\beta_2$-adrenergic receptors in bronchial and vascular muscle.

The compounds of the instant invention also include those of Formula X

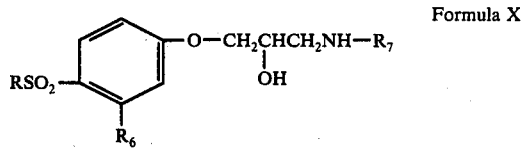

Formula X and pharmaceutical non-toxic acid addition salts thereof wherein
R is lower alkyl;
$R_6$ is hydrogen or lower alkyl of 1 to 4 carbon atoms inclusive; and
$R_7$ is an aryloxy radical having the formula

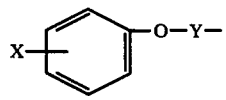

wherein the symbol "X" is 3,4-methylenedioxy or "X" is located in the 2-, 3-, or 4-position and is hydrogen, hydroxy, lower alkyl of 1 to 4 carbon atoms inclusive, halogen (including chlorine, bromine, fluorine and iodine), straight or branched chain alkoxy of 1 to 4 carbon atoms inclusive), or di-(straight or branched chain alkoxy of 1 to 4 carbon atoms inclusive), and the symbol "Y" is an alkylene radical of 2 to 4 carbon atoms inclusive such as $-CH(CH_3)-$, $-CH_2CH(CH_3)-$, $-CH_2CH_2-$, $-CH_2C(CH_3)_2-$, $-(CH_2)_3-$, and the like.

Other contemplated classes of compounds within the ambit of Formula X are those wherein (a) R is lower alkyl, $R_6$ is lower alkyl, and $R_7$ is as defined above;
(b) R is lower alkyl, $R_6$ is hydrogen, and $R_7$ is as defined above;
(c) R is methyl, $R_6$ is hydrogen, and $R_7$ is as defined above;
(d) R is methyl, $R_6$ is lower alkyl, and $R_7$ is as defined above;
(e) R is lower alkyl, $R_6$ is methyl and $R_7$ is as defined above;
(f) R is methyl, $R_6$ is methyl, and $R_7$ is as defined above;
(g) R is lower alkyl, $R_6$ is lower alkyl, and $R_7$ is selected from the group consisting of phenoxyethyl, phenoxyisopropyl, and phenoxy-t-butyl;
(h) R is lower alkyl, $R_5$ is hydrogen, and $R_6$ is selected from the group consisting of phenoxyethyl, phenoxyisopropyl, and phenoxy-t-butyl;
(i) R is lower alkyl, $R_5$ is methyl, and $R_6$ is selected from the group consisting of phenoxyethyl, phenoxyisopropyl, and phenoxy-t-butyl;
(j) R is methyl, $R_5$ is lower alkyl, and $R_6$ is selected from the group consisting of phenoxyethyl, phenoxyisopropyl, and phenoxy-t-butyl;
(k) R is methyl, $R_5$ is hydrogen, and $R_6$ is selected from the group consisting of phenoxyethyl, phenoxyisopropyl, and phenoxy-t-butyl;
(l) R is methyl, $R_5$ is methyl, and $R_6$ is selected from the group consisting of phenoxyethyl, phenoxyisopropyl, and phenoxy-t-butyl;

(m) R is lower alkyl, $R_5$ is lower alkyl, and $R_6$ is phenoxyisopropyl;

(n) R is lower alkyl, $R_5$ is methyl, and $R_6$ is phenoxyisopropyl;

(o) R is lower alkyl, $R_5$ is hydrogen, and $R_6$ is phenoxyisopropyl;

(p) R is lower alkyl, $R_5$ is lower alkyl, and $R_6$ is phenoxyethyl;

(q) R is lower alkyl, $R_5$ is methyl, and $R_6$ is phenoxyethyl; and (r) R is lower alkyl, $R_5$ is hydrogen, and $R_6$ is phenoxyethyl.

The compounds of Formula X are prepared in a manner analogous to those of Formula I by substituting a phenol derivative of Formula XI

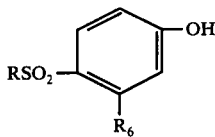

Formula XI for that of Formula II and an amine of Formula XII

 Formula XII for an amine of Formula IV or a compound of Formula XIII

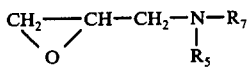 Formula XIII for a compound of Formula VII. In foregoing Formulas XI-XIII, the symbols "R, $R_5$, $R_6$ and $R_7$" are as previously defined.

For the purpose of treating hypertension in a mammal, the antihypertensive process of the instant invention is carried out by systemically administering to a mammal in need of such treatment an antihypertensive effective amount of a compound selected from the group characterized by Formula I or preferably by Formula X or a pharmaceutically acceptable non-toxic acid addition salt thereof. By systemic administration, it is intended to include both oral and parenteral routes. Examples of parenteral administration are intramuscular, intravenous, intraperitoneal, rectal, and subcutaneous administration. The dosage will vary with the form of administration and the particular compound chosen. However, from about 0.3 mg. per kg. body weight to 100 mg. per kg. body weight of a compound characterized by Formula I administered in effective single or multiple dosage units is generally satisfactory. In accordance with conventional clinical practice, the antihypertensive agent is administered at a dosage substantially less than the dose of the compound thought to be effective. Thereafter, the dosage is increased by small increments until the optimum antihypertensive effect under the circumstances is reached. At effective antihypertensive dosage levels, the compounds of this invention are substantially free of harmful or deleterious side effects. The compounds of Formula X are particularly distinguished as antihypertensive agents in having a rapid onset of action. In the spontaneous hypertensive rat (an in vivo animal model considered predictive of antihypertensive utility), an oral dose of 100 mg./kg. body weight of 3-[4-(methylsulfonyl)-m-tolyloxy]-1-(1-phenoxy-2-propylamino)-2-propanol lowered blood pressure by about 22.4 mm Hg.

With respect to cardioselective β-adrenergic blocking activity, the most preferred groups comprise those compounds of Formula Ic or Formula IX and pharmaceutically acceptable acid addition salts thereof wherein R is lower alkyl of 1 to 4 carbon atoms inclusive, $R_1$ is cyclopropyl or a branched chain alkyl group of 3 or 4 carbon atoms inclusive, $R_3$ is lower alkyl of 1 to 4 carbon atoms inclusive, and $R_4$ is lower alkylsulfonyl of 1 to 4 carbon atoms inclusive.

The antiarrhythmic effects of the compounds of the present invention characterized by Formula I and Formula X can be demonstrated in standard in vitro pharmacological tests such as the electrically stimulated isolated rabbit atrium as well as in intact experimental animals. For instance, 1-(isopropylamino)-3-[2-(methylsulfonyl)-phenoxy]-2-propanol hydrochloride reverses experimentally-induced ventricular tachycardia in the dog at an intravenous dose of from 1-4 mg./kg. body weight.

For the purpose of exerting an antiarrhythmic or cardioselective $β_1$-adrenergic blocking effect in a mammal having need thereof, an effective dose ranging from 0.05 mg. per kilogram body weight to 20 mg. per kilogram body weight of an alkylsulfonylphenoxypropanolamine characterized by Formula I or Formula X is administered orally or parenterally to the mammal. Preferably, the compounds of the invention are administered to the mammal in an effective amount sufficient to restore mammal cardiac rhythm or reduce the inotropic, chronotropic effect of β-adrenergic agonists without appreciably affecting the β-adrenergic receptors in the mammalian smooth muscle tissue.

The alkylsulfonylphenoxypropanolamines of Formula I and Formula X may be compounded and formulated with organic or inorganic solid materials or liquids which are pharmaceutically acceptable carriers to provide pharmaceutical compositions of unit dosage form suitable for administration to mammals. Pharmaceutical compositions may take the form of tablets, capsules, powder, granules, suspensions, solutions and the like. Suitable pharmaceutical carriers comprise both solids and liquids such as corn starch, lactose, calcium phosphate, stearic acid, polyethyleneglycol, water, sesame seed oil, peanut oil, propyleneglycol, and so forth. Standard formulating procedures are employed to prepare the pharmaceutical compositions.

The following examples illustrate the preparation of specific compounds having β-adrenergic cardioselective blocking activity and should not be construed as a limitation of the invention.

The nuclear magnetic spectral data reported herein includes the chemical shifts (δ) in parts per million, the multiplicity for that shift including the coupling constant (Hz = J value) when appropriate, and the relative area under the curve for each chemical shift which corresponds to the number of protons. Multiplicity symbols are: s, singlet; bs, broad singlet; d, doublet; and m, multiplet. Tetramethylsilane was used as the internal reference.

EXAMPLE 1

(a) A mixture of 4-(methylsulfonyl)-m-cresol (18.6 g., 0.1 mole), epichlorohydrin (60 g., 0.65 mole) and 0.6 g. of pyrrolidine is heated on steam bath for 12 hr. Excess epichlorohydrin is removed under reduced pressure, the resulting chlorohydrin derivative taken up in 50 ml. of absolute ethanol and filtered through diatomaceous earth. Isopropylamine (50 g., 0.85 mole) and 0.1 g. of potassium iodide are added to the ethanol filtrate of the epichlorohydrin derivative and the mixture is refluxed for 18 hr. and filtered. Concentration of the filtrate under reduced pressure affords a residue which is taken up in 70 ml. of 1N hydrochloric acid and 300 ml. of absolute ethanol. Distillables are removed under reduced pressure and the resulting residue stirred with ether to provide solid crude product. Crystallization of the crude product from butanone-methanol and again from 95% ethanol-ether, affords 1-(ISO-PROPYLAMINO)-3-[4-(METHYLSULFONYL)-m-TOLYLOXY]-2-PROPANOL HYDROCHLORIDE, m.p. 177.0°–179.0° C. (corr.) in a 62% overall yield. A sample, m.p. 176.0°–178.0° C. (corr), analyzed as follows.

Analysis. Calcd. for $C_{14}H_{23}NO_4 \cdot HCl$: C, 49.77; H, 7.16; N, 4.15. Found: C, 49.72; H, 7.16; N, 4.08.

Nuclear Magnetic Resonance, DMSO-$d_6$, $\delta$(ppm): 1.28 [d, 6.5 Hz, 6H]; 2.58 [s, 3H]; 3.11[s, 3H]; 3.13 [m, 3H]; 4.11 [m, 3H]; 7.01 [m, 2H]; 7.77 [d, 9.2 Hz, 1H]; 8.9 [bs, 2H].

(b) A modification of the procedure for preparing 1-(isopropylamino)-3-[4-(methylsulfonyl)-m-tolyloxy]-2-propanol employing aqueous sodium hydroxide as the reaction medium follows. Epichlorohydrin (37 g., 0.4 mole) is added portionwise in 5 min. to a solution of 4-(methylsulfonyl)-m-cresol (0.2 mole) and sodium hydroxide (13 g., 0.32 mole) in 250 ml. of water at 30° C. Stirring is continued for 24 hr. and the final pH of the solution is 8–8.5. The reaction mixture extracted with two 250 ml. portions of chloroform, the chloroform extract dried over sodium carbonate, filtered and the filtrate concentrated under reduced pressure provides the crude epichlorohydrin derivative. The epichlorohydrin derivative is taken up in 150 ml. of ethanol and treated with isopropylamine (17 g., 0.286 mole) in 20 ml. of water. After stirring for 10 min., the mixture is refluxed for 4 hr. and distillables removed under reduced pressure. The residue taken up in ethanol and acidified with ethanolic hydrogen chloride affords 1-(ISO-PROPYLAMINO)-3-[4-(METHYLSULFONYL)-m-TOLYLOXY]-2-PROPANOL HYDROCHLORIDE.

(c) A further modification of the procedure for preparing 1-(isopropylamino)-3-[4-methylsulfonyl)-m-tolyloxy]-2-propanol employing an epihalohydrin derivative of Formula VII containing a hydrogenolyziable blocking group follows. 1-[(N-Benzyl)isopropylamino]-2,3-epoxypropane is reacted with 4-(methylsulfonyl)-m-cresol sodium salt in ethanol to provide 1-[(N-benzyl)isopropylamino]-3-[4-(methylsulfonyl)-m-tolyloxy]-2-propanol.

The reaction mixture is filtered, acidified with ethanolic hydrogen chloride and the benzyl blocking group removed by catalytic hydrogenation employing palladium-on-charcoal catalyst. The catalyst is collected and the filtrate concentrated to provide 1-(ISO-PROPYLAMINO)-3-[4-(METHYLSULFONYL)-m-TOLYLOXY]-2-PROPANOL HYDROCHLORIDE.

EXAMPLE 2

Reaction of the chlorohydrin derivative of 4-(methylsulfonyl)-m-cresol with tert.-butylamine according to the procedure of Example 1 (a) affords 1-(tert.-BUTYLAMINO)-3-[4-(METHYLSULFONYL)-m-TOLYLOXY]-2-PROPANOL HYDROCHLORIDE, m.p. 175.0°–176.0° C. (resolidifying and remelting at 197.0° C.)(corr.), from acetonitrile.

Analysis. Calcd. for $C_{15}H_{25}NO_4S \cdot HCl$: C, 51.20; H, 7.45; N, 3.98. Found: C, 50.99; H, 7.72; N, 4.20.

Nuclear Magnetic Resonance, DMSO-$d_6$, $\delta$(ppm): 1.31 [s, 9H]; 2.59 [s, 3H]; 3.02 [m, 2H]; 3.11 [s, 3H]; 4.10 [m, 3H]; 6.97 [m, 2H]; 7.75 [d, 9.5 Hz, 1H]; 8.7 [bs, 2H].

EXAMPLE 3

Reaction of the chlorohydrin derivative of 4-(methylsulfonyl)phenol with isopropylamine according to the procedure of Example 1 (a) affords 1-(ISO-PROPYLAMINO)-3-[4-(METHYLSULFONYL)-PHENOXY]-2-PROPANOL HYDROCHLORIDE, m.p. 193.0°–195.0° C., from ethanol.

Analysis. Calcd. for $C_{13}H_{21}NO_4S \cdot HCl$: C, 48.22; H, 6.85; N, 4.32. Found: C, 48.00; H, 7.02; N, 4.25.

Nuclear Magnetic Resonance, DMSO-$d_6$, $\delta$(ppm): 1.28 [d, 6.5 Hz, 6H]; 3.12 [m, 3H]; 3.14 [s, 3H]; 4.13 [m, 3H]; 5.91 [d, 4.2 Hz, 1H]; 7.13 [m, 2H]; 7.80 [m, 2H]; 8.9 [bs, 2H].

EXAMPLE 4

Reaction of the chlorohydrin derivative of 4-(methylsulfonyl)-o-cresol with isopropylamine according to the procedure of Example 1 (a) affords 1-(ISO-PROPYLAMINO)-3-[4-(METHYLSULFONYL)-o-TOLYLOXY]-2-PROPANOL as the free base, m.p. 118.0°–120.0° C., from butanone.

Analysis. Calcd. for $C_{14}H_{23}NO_4S$: C, 55.79; H, 7.69; N, 4.65. Found: C, 56.00; H, 7.68; N, 4.42.

Nuclear Magnetic Resonance, CDCl$_3$, $\delta$(ppm): 1.10 [d, 6.4 Hz, 6H]; 2.27 [s, 3H]; 2.50 [bs, 2H]; 2.85 [m, 3H]; 2.99 [s, 3H]; 4.11 [m, 3H]; 6.86 [d, 9.3 Hz, 1H]; 7.65 [m, 2H].

EXAMPLE 5

Reaction of the chlorohydrin derivative of 4-(methylsulfonyl)phenol with tert.-butylamine according to the procedure of Example 1 (a) affords 1-(tert.-BUTYLAMINO)-3-[4-(METHYLSULFONYL)-PHENOXY]-2-PROPANOL HYDROCHLORIDE.

Analysis. Calcd. for $C_{14}H_{23}NO_4S \cdot HCl$: C, 49.77; H, 7.16; N, 4.15. Found: C, 50.10; H, 7.33; N, 4.00.

EXAMPLE 6

Reaction of the chlorohydrin derivative of 4-(methylsulfonyl)-m-cresol with cyclopropylamine according to the procedure of Example 1 (a) affords 1-(CYCLO-PROPYLAMINO)-3-[4-(METHYLSULFONYL)-m-TOLYLOXY]-2-PROPANOL HYDROCHLORIDE.

Analysis. Calcd. for $C_{14}H_{21}NO_4S \cdot HCl$: C, 50.07; H, 6.60; N, 4.17. Found: C, 50.23; H, 6.76; N, 4.02.

EXAMPLE 7

Reaction of chlorohydrin derivative of 4-(methylsulfonyl)-m-cresol with phenoxyisopropylamine according to the procedure of Example 1 (a) affords 1-(PHENOXYISOPROPYLAMINO)-3-[4-(METHYL-SULFONYL)-m-TOLYLOXY]-2-PROPANOL.

Analysis. Calcd. for $C_{20}H_{27}NO_5S$: C, 61.05; H, 6.92; N, 3.56. Found: C, 61.12; H, 7.14, N, 3.32.

EXAMPLE 8

Reaction of the chlorohydrin derivative of 2-(methylsulfonyl)phenol with isopropylamine according to the procedure of Example 1 (a) affords 1-(ISO-

PROPYLAMINO)-3-[2-(METHYLSULFONYL)-PHENOXY]-2-PROPANOL HYDROCHLORIDE.

Analysis. Calcd. for $C_{13}H_{21}NO_4S \cdot HCl$: C, 48.22; H, 6.85; N, 4.32. Found: C, 48.19; H, 7.05; N, 4.37.

EXAMPLE 9

Reaction of the chlorohydrin derivative of 4-(methylsulfonyl)-m-cresol with cyclopentylamine according to the procedure of Example 1 (a) affords 1(CYCLOPENTYLAMINO)-3-[4-(METHYLSULFONYL)-m-TOLYLOXY]-2-PROPANOL HYDROCHLORIDE, m.p. 183.0°–185.0° C. (corr.).

Analysis. Calcd. for $C_{16}H_{25}NO_4S \cdot HCl$: C, 52.81; H, 7.20; N, 3.85. Found: C, 53.04; H, 7.37; N, 3.69.

Nuclear Magnetic Resonance, DMSO-$d_6$, δ(ppm): 1.70 [m, 9H]; 2.58 [s, 3H]; 3.12 [s, 3H]; 3.15 [m, 3H]; 4.10 [m, 3H]; 5.84 [bs, 1H]; 6.94 [m, 2H]; 7.76 [d, 9.5 Hz, 1H]; 9.0 [bs, 2H].

EXAMPLE 10

Reaction of the chlorohydrin derivative of 4-(sec.-butylsulfonyl)phenol with isopropylamine according to the procedure of Example 1 (a) affords 1-(ISOPROPYLAMINO)-3-[4-(sec.-BUTYLSULFONYL)-PHENOXY]-2-PROPANOL.

EXAMPLE 11

Reaction of the chlorohydrin derivative of 4-(isopropylsulfonyl)-m-cresol with tert.-butylamine according to the procedure of Example 1 (a) affords 1-tert.-BUTYLAMINO)-3-[4-(ISOPROPYLSULFONYL)-m-TOLYLOXY]-2-PROPANOL.

EXAMPLE 12

Reaction of the chlorohydrin derivative of 4-(methylsulfonyl)-3-isopropylphenol with isopropylamine according to the procedure of Example 1 (a) affords 1-(ISOPROPYLAMINO)-3-[4-(METHYLSULFONYL)-3-ISOPROPYLPHENOXY]-2-PROPANOL.

EXAMPLE 13

In accordance with the procedure of Example 1(a), the chlorohydrin derivative of 4-(methylsulfonyl)-m-cresol obtained from 4-(methylsulfonyl)-m-cresol (7.0 g., 0.038 mole) and epichlorohydrin (22.6 g., 0.22 mole) is reacted with 4-methoxy-α,α-dimethylphenethylamine (13.5 g., 0.075 mole) to provide 1[(4-METHOXY-α,α-DIMETHYLPHENETHYL)AMINO]-3-[4-(METHYLSULFONYL)-m-TOLYLOXY]-2-PROPANOL HYDROCHLORIDE, m.p. 186°–187° C. (corr.), from acetone.

Analysis. Calcd. for $C_{22}H_{31}NO_5S \cdot HCl$: C, 57.69; H, 7.04; N, 3.06. Found: C, 57.67; H, 7.23; N, 2.86.

EXAMPLE 14

In accordance with the procedure of Example 1(a) the chlorohydrin derivative obtained from 4-(methylsulfonyl)-m-cresol (7.0 g., 0.038 mole) and epichlorohydrin (22.6 g., 0.022 mole) is reacted with 4-benzyloxy-α,α-dimethylphenethylamine (7.97 g., 0.033 mole) to provide 1-[(4-BENZYLOXY-α,α-DIMETHYLPHENETHYL)AMINO]-3-[4-(METHYLSULFONYL)-m-TOLYLOXY]-2-PROPANOL HYDROCHLORIDE.

A solution of 1-[(4-benzyloxy-α,α-dimethylphenethyl)amino]-3-[4-(methylsulfonyl)-m-tolyloxy]-2-propanol (6.45 g., 0.12 mole) in 250 ml. of methanol is hydrogenated employing 4.0 g. of 10% palladium on carbon catalyst. When reduction is complete, the catalyst is collected and the filtrate concentrate under reduced pressure to provide a residual solid. Crystallization of the crude solid from acetone affords analytically pure 1-[(4-HYDROXY-α,α-DIMETHYLPHENETHYL)AMINO]-3-[4-(METHYLSULFONYL)-m-TOLYLOXY]-2-PROPANOL HYDROCHLORIDE, m.p. 205.0° C. (with partial melt at 110.0°–115.0° C.).

Analysis. Calcd. for $C_{24}H_{29}NO_5S \cdot HCl$: C, 56.81; H, 6.81; N, 3.15. Found: C, 56.70; H, 6.73; N, 2.95.

EXAMPLE 15

The chlorohydrin derivative (0.048 mole) of 4-(methylsulfonyl)-m-cresol obtained from 4-(methylsulfonyl)-m-cresol and epichlorohydrin is reacted with phenoxyethylamine (6.6 g., 0.048 mole) at 160° C. for a period of 30 min. to provide 3-[4-(METHYLSULFONYL)-m-TOLYLOXY]-1-(2-PHENOXYETHYL)AMINO-2-PROPANOL HYDROCHLORIDE, m.p. 184.0°–186.0° C. (corr.), from methanol:isopropanol.

Analysis. Calcd. for $C_{19}H_{25}NO_5S \cdot HCl$: C, 54.86; H, 6.30; N, 3.37. Found: C, 54.82; H, 6.15; N, 3.28.

EXAMPLE 16

The chlorohydrin derivative (0.047 mole) of 4-(methylsulfonyl)-m-cresol obtained from 4-(methylsulfonyl)-m-cresol and epichlorohydrin is reacted with 1,1-dimethyl-2-phenoxyethylamine (7.84 g., 0.047 mole) at a temperature of 160° C. for a period of 30 min. to provide 1-[(1,1-DIMETHYL-2-PHENOXYETHYL)AMINO]-3-[4-(METHYLSULFONYL)-m-TOLYLOXY]-2-PROPANOL, m.p. 117.5°–120.5° C. from acetonitrile.

Analysis. Calcd. for $C_{21}H_{29}NO_5S$: C, 61.89; H, 7.17; N, 3.44. Found: C, 61.81; H, 7.08; N, 3.39.

EXAMPLE 17

Following the procedure of Example 15 but employing equimolar amounts of the following phenoxyalkylamines:

o-methylphenoxyethylamine,
m-methylphenoxyethylamine,
p-methylphenoxyethylamine,
2-(3,4-dimethylphenoxy)ethylamine,
o-chlorophenoxyethylamine,
m-chlorophenoxyethylamine,
p-chlorophenoxyethylamine,
m-bromophenoxyethylamine,
p-bromophenoxyethylamine,
p-methoxyphenoxyethylamine,
2-(3,4-dimethoxyphenoxy)ethylamine,
2-(3,4-methylenedioxyphenoxy)ethylamine, respectively in place of phenoxyethylamine there is produced:

(a) 3-[4-(methylsulfonyl)-m-tolyloxy]-1-[2-(o-methylphenoxy)ethyl]amino-2-propanol,
(b) 3-[4-(methylsulfonyl)-m-tolyloxy]-1-[2-(m-methylphenoxy)ethyl]amino-2-propanol,
(c) 3-[4-(methylsulfonyl)-m-tolyloxy]-1-[2-(p-methylphenoxy)ethyl]amino-2-propanol,
(d) 3-[4-(methylsulfonyl)-m-tolyloxy]-1-[2-(3,4-dimethylphenoxy)ethyl]amino-2-propanol,
(e) 3-[4-(methylsulfonyl)-m-tolyloxy]-1-[2-(o-chlorophenoxy)-ethyl]amino-2-propanol,
(f) 3-[4-(methylsulfonyl)-m-tolyloxy]-1-[2-(m-chlorophenoxy)-ethyl]amino-2-propanol, (g) 3-[4-(methylsulfonyl)-m-tolyloxy]-1-[2-(p-chlorophenoxy)-ethyl]amino-2-propanol,
(h) 3-[4-(methylsulfonyl)-m-tolyloxy]-1-[2-(m-bromophenoxy)-ethyl]amino-2-propanol,
(i) 3-[4-(methylsulfonyl)-m-tolyloxy]-1-[2-(p-bromophenoxy)-ethyl]amino-2-propanol,
(j) 3-[4-(methylsulfonyl)-m-tolyloxy]-1-[2-(p-methoxyphenoxy)ethyl]amino-2-propanol,
(k) 3-[4-(methylsulfonyl)-m-tolyloxy]-1-[2-(3,4-dimethoxyphenoxy)ethyl]amino-2-propanol,
(l) 3-[4-(methylsulfonyl)-m-tolyloxy]-1-[2-(3,4-methylenedioxyphenoxy)ethyl]amino-2-propanol.

EXAMPLE 18

Following the procedure of Example 15, reaction of the equimolar amount of the chlorohydrin derivatives of 4-(methylsulfonyl)phenol with the following phenoxyalkylamines:
phenoxyethylamine,
phenoxyisopropylamine,
phenoxy-t-butylamine,
o-methylphenoxyethylamine,
m-methoxyphenoxyethylamine,
p-methylphenoxyethylamine,
2-(3,4-dimethylphenoxy)ethylamine,
o-chlorophenoxyethylamine,
m-chlorophenoxyethylamine,
p-chlorophenoxyethylamine,
m-bromophenoxyethylamine,
p-bromophenoxyethylamine,
p-methoxyphenoxyethylamine,
2-(3,4-dimethoxyphenoxy)ethylamine,
2-(3,4-methylenedioxyphenoxy)ethylamine,
provides, respectively, the following products:
(a) 3-[4-(methylsulfonyl)phenoxy]-1-(2-phenoxyethyl)-amino-2-propanol,
(b) 3-[4-(methylsulfonyl)phenoxy]-1-(1-phenoxy-2-propylamino)-2-propanol,
(c) 3-[4-(methylsulfonyl)phenoxy]-1-[(1,1-dimethyl-2-phenoxyethyl)amino]-2-propanol,
(d) 3-[4-(methylsulfonyl)phenoxy]-1-[2-(o-methylphenoxy)ethyl]amino-2-propanol,
(e) 3-[4-(methylsulfonyl)phenoxy]-1-[2-(m-methylphenoxy)-ethyl]amino-2-propanol,
(f) 3-[4-(methylsulfonyl)phenoxy]-1-[2-(p-methylphenoxy)-ethyl]amino-2-propanol,
(g) 3-[4-(methylsulfonyl)phenoxy]-1-[2-(3,4-dimethylphenoxy)-ethyl]amino-2-propanol,
(h) 3-[4-(methylsulfonyl)phenoxy]-1-[2-(o-chlorophenoxy)-ethyl]amino-2-propanol,
(i) 3-[4-(methylsulfonyl)phenoxy]-1-[2-(m-chlorophenoxy)-ethyl]amino-2-propanol,
(j) 3-[4-(methylsulfonyl)phenoxy]-1-[2-(p-chlorophenoxy)-ethyl]amino-2-propanol,
(k) 3-[4-(methylsulfonyl)phenoxy]-1-[2-(m-bromophenoxy)ethyl]amino-2-propanol,
(l) 3-[4-(methylsulfonyl)phenoxy]-1-[2-(p-bromophenoxy)-ethyl]amino-2-propanol,
(m) 3-[4-(methylsulfonyl)phenoxy]-1-[2-(p-methoxyphenoxy)-ethyl]amino-2-propanol,
(n) 3-[4-(methylsulfonyl)phenoxy]-1-[2-(3,4-dimethoxyphenoxy)-ethyl]amino-2-propanol,
(o) 3-[4-(methylsulfonyl)phenoxy]-1-[2-(3,4-methylenedioxyphenoxy)ethyl]amino-2-propanol.

EXAMPLE 19

Reaction of the chlorohydrin derivative of 4-(methylsulfonyl)-m-cresol with p-benzyloxyphenoxyethylamine in accordance with the procedure of Example 15 provides 3-[4-(methylsulfonyl)-m-tolyloxy]-1-[(p-benzyloxyphenoxyethyl)amino]-2-propanol.

The benzyloxy intermediate is debenzylated according to the procedure set forth in Example 14 to provide 3-[4-(METHYLSULFONYL)-m-TOLYLOXY]-1-[(p-HYDROXYPHENOXYETHYL)AMINO]-2-PROPANOL.

EXAMPLE 20

Reaction of the chlorohydrin derivative of 4-(methylsulfonyl)phenol with p-benzyloxyphenoxyethylamine in accordance with the procedure of Example 15 provides 3-[4-(METHYLSULFONYL)PHENOXY]-1-[(p-BENZYLOXYPHENOXYETHYL)AMINO]-2-PROPANOL.

The benzyloxy intermediate is debenzylated according to the procedure set forth in Example 14 to provide 3-[4-(METHYLSULFONYL)PHENOXY]-1-[(p-HYDROXYPHENOXYETHYL)AMINO]-2-PROPANOL.

What is claimed is:

1. A process for treating hypertension which comprises systemically administering to a mammal in need of said treatment an antihypertensive effective amount of a compound selected from the group consisting of
1-(phenoxyisopropylamino)-3-[4-(methylsulfonyl)-m-tolyxyl 2-propanol, and
3-[4-(methylsulfonyl)-m-tolyloxy]-1-(2-phenoxyethyl)amino-2-propanol
or a pharmaceutically acceptable non-toxic acid addition salt thereof.

2. The process of claim 1 wherein said compound is 1-(phenoxyisoproylamino)-3-[4-(methylsulfonyl)-*m*-tolyloxy]-2-propanol hydrochloride.

3. The process of claim 1 wherein said compound is 3-[4-(methylsulfonyl)-m-tolyloxy]-1-(2-phenoxyethyl)amino-2-propanol hydrochloride.

4. A process which comprises systemically administering to a mammal in need of antiarrhythmic treatment an antiarrhythmic effective amount of a compound selected from the group consisting of
1-(isopropylamino)-3-[2-(methylsulfonyl)phenoxy]-2-propanol and
1-[(4-(methoxy-α,α-dimethylphenethyl)amino]-3-[4-(methylsulfonyl)-m-tolyloxy]-2-propanol
or a pharmaceutically acceptable non-toxic acid addition salt thereof.

5. The process of claim 4 wherein said compound is 1-(isopropylamino)-3-[2-(methylsulfonyl)phenoxy]-2-propanol hydrochloride.

6. The process of claim 4 wherein said compound is 1-[(4-methoxy-α,α-dimethylphenethyl)amino]-3-[4-(methylsulfonyl)-m-tolyloxy]-2-propanol hydrochloride.

* * * * *